(12) United States Patent
Kulesza

(10) Patent No.: US 8,415,389 B2
(45) Date of Patent: Apr. 9, 2013

(54) POLYPHENOL-BASED COMPOSITION, AND METHODS AND SYSTEMS FOR ITS PREPARATION

(76) Inventor: John E. Kulesza, Wethersfield, CT (US)

( * ) Notice: Subject to any disclaimer, the term of this patent is extended or adjusted under 35 U.S.C. 154(b) by 1172 days.

(21) Appl. No.: 12/022,391

(22) Filed: Jan. 30, 2008

(65) Prior Publication Data

US 2008/0181860 A1 Jul. 31, 2008

Related U.S. Application Data

(60) Provisional application No. 60/887,399, filed on Jan. 31, 2007.

(51) Int. Cl.
*A61K 31/353* (2006.01)
*A61K 8/18* (2006.01)
*A61K 8/34* (2006.01)
*A61K 8/49* (2006.01)
*A61K 47/10* (2006.01)
*A61K 47/14* (2006.01)
*A61K 47/20* (2006.01)
*A61K 8/37* (2006.01)
*A61K 8/46* (2006.01)

(52) U.S. Cl. ......... 514/456; 424/401; 514/772; 514/785

(58) Field of Classification Search .................. None
See application file for complete search history.

(56) References Cited

U.S. PATENT DOCUMENTS 5,140,043 A * 8/1992 Darr et al. ..................... 514/474
6,013,637 A * 1/2000 Klein et al. ..................... 514/43

FOREIGN PATENT DOCUMENTS

WO WO 2005087224 A1 * 9/2005

OTHER PUBLICATIONS

CAS Registry No. 107-88-0 (Nov. 16, 1984).*
INCI Directory (entry for ethoxydiglycol). http://www.specialchem4cosmetics.com/services/inci/ingredientaspx?id=4598; downloaded Sep. 10, 2011).*
CAS Registry No. 111-90-0 (Nov. 16, 1984).*
"Green Tea and the Skin" Hsu; Journal of the American Academy of Dermatology; 1049-1059, (Jun. 2005).
"Preformulation Study of Epigallocatechin Gallate, a Promising Antioxidant for Topical Skin Cancer Prevention", Proniuk, et al; Journal of Pharmaceutical Sciences, 111-116, vol. 91, No. 01 (Jan. 2002).
Pharmacokinetics of the Green Tea Derivative EGCG, by the Topical Route of Administration in Mouse and Human Skin; Dvorakova et al; Cancer Chemother Pharmacal 43: 331-335 (1999).

* cited by examiner

*Primary Examiner* — Daniel Sullivan
*Assistant Examiner* — Peter Anthopolos
(74) *Attorney, Agent, or Firm* — Gifford, Krass, Sprinkle, Anderson & Citkowski, P.C.

(57) ABSTRACT

A system for preparing a polyphenol containing formulation includes a first component which is a polyphenol and a second component which is the solvent system for the polyphenol. The solvent system includes water and a surfactant which is an ester of a dicarboxylic acid. The components are maintained separately from one another and are mixed prior to use. Specific compositions prepared through the use of the system include polyphenols and a solvent system based upon diaryl sulfosuccinate salts, water and optional glycols together with ancillary ingredients such as buffers, preservatives, coloring agents, fragrances, and thickeners.

1 Claim, No Drawings

POLYPHENOL-BASED COMPOSITION, AND METHODS AND SYSTEMS FOR ITS PREPARATION

CROSS REFERENCE TO RELATED APPLICATIONS

This application claims priority of U.S. Provisional Patent Application Ser. No. 60/887,399 filed Jan. 31, 2007, entitled "Polyphenol-Based Composition, and Methods and Systems for its Preparation" which is incorporated herein by reference.

FIELD OF THE INVENTION

This invention relates generally to topical dermatological compositions. More specifically, the invention relates to topical dermatological compositions based upon polyphenols. Most specifically, the invention relates to stable, topical dermatological compositions based upon polyphenols, and to methods and systems for their preparation.

BACKGROUND OF THE INVENTION

Polyphenols are organic molecules comprising one or more aromatic nuclei having a plurality of hydroxyl groups dependent therefrom. Polyphenols are found in a variety of plant materials. One particular source of polyphenols comprises green tea, and one particular green tea derived polyphenol having high levels of activity is epigallocatechin gallate (EGCG).

Polyphenols, and green tea polyphenols in particular, have been shown to have a number of beneficial effects on the skin when applied topically. These materials have been shown to reduce skin inflammation and accelerate wound healing. In addition, polyphenols have an antioxidant effect which can reduce or alleviate skin damage resultant from aging, light exposure, chemical exposure and the like. Polyphenols have also been demonstrated to prevent or inhibit carcinogenesis, and these materials can function as ultraviolet protective agents.

In view of the foregoing, there is significant interest in the use of EGCG and other polyphenols as topical dermatological treatments. However, such polyphenolic compounds tend to be highly reactive, and hence they have poor long-term stability when disposed in solutions. Also, EGCG and like materials are fairly hydrophilic, and this inhibits their ability to penetrate the hydrophobic upper layers of the epidermis, primarily the stratum corneum, as well as the deeper, living layers. Hence, surfactants are needed to temporarily disrupt these layers so as to allow the penetration of hydrophilic polyphenols such as EGCG. Unfortunately, EGCG and other such polyphenols very often interact adversely with most surfactants and other components of solutions so as to cause precipitation, clouding, or other unwanted conditions. The foregoing problems have greatly limited the use of polyphenols in therapeutic compositions. As will be described in detail hereinbelow, the present invention is directed to compositions, methods and systems which allow for the preparation of polyphenol-based compositions which are stable in solution and have the ability to penetrate the skin; and hence overcome the foregoing problems.

BRIEF DESCRIPTION OF THE INVENTION

Disclosed is a system for preparing a polyphenol containing formulation. The system includes a first and a second component. The first component is a polyphenol. The second component is a solvent system for the polyphenol and comprises water and a surfactant which is an ester of a dicarboxylic acid. The first and second components are maintained separately from one another and are mixable so as to provide a solution of the polyphenol in the solvent at or near the time of use. The polyphenol may be stored under an inert atmosphere such as a nitrogen atmosphere and in particular instances comprises a green tea polyphenol such as epigallocatechin gallate. The solvent system may further include a glycol and may optionally include buffers, preservatives, coloring agents, fragrances and thickeners.

In particular instances, the surfactant is a diaryl sodium sulfosuccinate such as dioctyl sodium sulfosuccinate.

Also disclosed is a method for preparing the composition through the use of the system. Further disclosed are some specific compositions.

DETAILED DESCRIPTION OF THE INVENTION

The present invention, in one aspect, provides a system which allows for the preparation of polyphenol-based therapeutic compositions. The system has a very long shelf life since the polyphenol component is stored, in a dry form, separately from the solvent portion of the composition. Furthermore, the present invention provides a unique solvent system which is compatible with, and stabilizes, the polyphenol. In use, the polyphenol is dissolved in the solvent at, or near, the point of use or dispensing. The resultant composition may then be stored for a reasonable period of time without undue loss of potency.

In particular embodiments, the system includes a first component which is the polyphenol, such as EGCG, disposed in a container such as a vial, bag, or the like. The polyphenol may be stored under an inert atmosphere such as a nitrogen atmosphere to prevent unwanted interactions with oxygen, moisture or the like. The system includes a second component which is a solvent for the polyphenol. The solvent will, in particular embodiments, comprise water and a surfactant. In particular aspects of this invention, the surfactant is an ester of a dicarboxylic acid. It has been found that such surfactants provide a clear, stable solution of the polyphenol. This is in contrast to various other classes of surfactants which tend to cause formation of a cloudy solution. One particular surfactant of the dicarboxylic acid ester type is dioctyl sodium sulfosuccinate, also known in the art as DSS or Docusate Sodium (INCI, USP). Other esters of succinic acid such as dihexyl or didecyl may likewise be employed, as may be esters of other diacids.

The solvent component may further include other materials, and one particular class of materials having utility in these compositions comprise glycols, including aryl glycols such as butylene glycol, propylene glycol and the like, as well as complex glycols such as ethoxydiglycol, glycerol and the like. The solvent component may further include well known preservative materials such as DMDM hydantoin, iodopropynyl butylcarbamate, and other such materials. Stabilizers such as edetate disodium may be included. Buffering agents may also be included as may be coloring agents, thickening agents, fragrances and the like.

In use, the polyphenol component is mixed with the solvent component so as to form a clear solution. The solution may then be provided directly to a patient for application to the skin, or in some instances, the solution may be imbibed upon an absorbent material such as absorbent applicator pads.

A variety of compositions may be prepared in accord with the foregoing. In general, the polyphenol component will comprise, on a weight basis, 1-15% of the composition and in certain instances 1-10% of the composition. (Unless otherwise noted, all percentages stated herein are on a weight basis.) The surfactant will typically comprise 0.1-1% of the composition, and water will comprise the bulk of the solvent. Additional solvent materials such as glycols will generally comprise 2-10% of the composition, while additional ingredients such as buffers, preservatives, stabilizers, fragrances, coloring agents, scents and the lice will comprise relatively minor proportions of the composition.

One specific class of compositions will comprise, on a weight basis, 1-15% of EGCG, 1-10% of butylene glycol, 1-10% of ethoxydialycol, and 0.1-1% of dioctyl sodium sulfosuccinate, with the balance of the composition comprising water. In those instances where preservatives are included, they will comprise approximately 0.05-0.5% of the composition. Edetate disodium or other stabilizers, when included, will comprise 0.01-0.1% by weight, and buffers, if utilized, will comprise a similar weight percentage.

One particular composition in accord with the present invention comprises, on a weight basis: 5% EGCG, 5% butylene glycol, 3% ethoxydiglycol, 0.3% dioctyl sodium sulfosuccinate, 0.2% of a preservative mixture of DMDM hydantoin and iodopropynyl butylcarbamate, 0.05% edetate disodium, and 0.7% of a citric acid/sodium citrate buffer. The remainder of the composition is water. This composition is prepared from a storage-stable system in which the EGCG is stored as a dry powder, under nitrogen, in a sealed vial, and the remainder of the components comprise a solvent stored in a separate bottle. Before use, the EGCG is added to the bottle of the aqueous vehicle and the mixture is shaken to form a clear, pink solution which, in particular instances, is poured over a jar of dry applicator pads. After compounding, the solution-saturated pads will retain at least 95% potency over a 60 day time period when stored in a cool dry place (less than 20° C.). Storage under refrigeration (approximately 4° C.) will prolong stability to approximately 90 days.

In use, the pads prepared in accord with the foregoing are used twice daily after cleansing. It has been found that in compositions of this type, the vehicle will additionally act as a toner to remove any soap residue, excess lipids and debris from the skin, while simultaneously depositing an EGCG substrate coating. This cleansing activity of the pad can improve penetration of the EGCG or other phenol into the skin; and thus, the pad further functions as a physical penetration enhancer.

In view of the foregoing, yet other compositions, formulations and methods will be apparent to those of skin in the art. It is to be understood that the foregoing is illustrative of specific features and embodiments of the present invention, but is not meant to be a limitation upon the practice thereof. It is the following claims, including all equivalents, which define the scope of the invention.

The invention claimed is:

1. An aqueous topical dermatological composition consisting essentially of, on a weight basis:
   1-15% epigallocatechin gallate;
   1-10% butylene glycol;
   1-10% ethoxydiglycol;
   0.1-1% dioctyl sodium sulfosuccinate; and
   optionally, one or more of a preservative, a buffer, a coloring agent, a fragrance, and a thickener; and
   water; whereby the composition is a clear solution.

* * * * *